(12) United States Patent  (10) Patent No.: US 9,351,834 B2
McDaniel et al.  (45) Date of Patent: May 31, 2016

(54) NEGATIVE-POSITIVE PRESSURIZABLE IMPLANT

(75) Inventors: John M. McDaniel, Warsaw, IN (US); Nathan Winslow, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 676 days.

(21) Appl. No.: 13/608,155

(22) Filed: Sep. 10, 2012

(65) Prior Publication Data

US 2013/0211539 A1 Aug. 15, 2013

Related U.S. Application Data

(60) Provisional application No. 61/533,374, filed on Sep. 12, 2011.

(51) Int. Cl.
*A61F 2/28* (2006.01)
*A61F 2/40* (2006.01)
*A61F 2/30* (2006.01)

(52) U.S. Cl.
CPC ............... *A61F 2/28* (2013.01); *A61F 2/4003* (2013.01); *A61F 2002/2817* (2013.01); *A61F 2002/3068* (2013.01); *A61F 2002/3092* (2013.01); *A61F 2002/30332* (2013.01); *A61F 2002/30691* (2013.01); *A61F 2002/30884* (2013.01)

(58) Field of Classification Search
CPC .................. A61F 2/30677; A61F 2002/3068; A61F 2002/30673; A61F 2002/30691; A61F 2002/30693; A61F 2002/30548; A61F 2002/5032; A61F 2002/74; A61F 2002/3664; A61F 2002/3666; A61F 2002/3668; A61F 2/3662; A61F 2002/365; A61F 2002/3625; A61F 2/28; A61F 2/4003; A61F 2002/2817
See application file for complete search history.

(56) References Cited

U.S. PATENT DOCUMENTS

| | | | |
|---|---|---|---|
| 3,030,951 | A | 4/1962 | Mandarino |
| 4,274,163 | A | 6/1981 | Malcom et al. |
| 4,399,814 | A | 8/1983 | Pratt, Jr. et al. |
| 4,778,474 | A * | 10/1988 | Homsy ............... A61F 2/30767 623/22.14 |
| 5,059,175 | A | 10/1991 | Hanover et al. |
| 5,167,625 | A | 12/1992 | Jacobsen et al. |
| 5,316,550 | A | 5/1994 | Forte |
| 5,340,362 | A | 8/1994 | Carbone |
| 5,423,334 | A | 6/1995 | Jordan |
| 5,441,538 | A | 8/1995 | Bonutti |
| 5,514,137 | A | 5/1996 | Coutts |
| 5,681,289 | A | 10/1997 | Wilcox et al. |
| 5,683,395 | A | 11/1997 | Mikhail |
| 5,702,446 | A | 12/1997 | Schenck et al. |
| 5,891,101 | A | 4/1999 | Wilcox et al. |
| 5,895,375 | A | 4/1999 | Wilcox et al. |
| 5,958,314 | A | 9/1999 | Draenert |
| 6,087,553 | A | 7/2000 | Cohen et al. |
| 6,121,172 | A | 9/2000 | Marcolongo et al. |

(Continued)

FOREIGN PATENT DOCUMENTS

| | | |
|---|---|---|
| DE | 3704089 | 8/1988 |
| EP | 0 958 789 | 11/1999 |
| WO | WO 03/086241 | 10/2003 |

*Primary Examiner* — Christopher D Prone
(74) *Attorney, Agent, or Firm* — Schwegman Lundberg & Woessner, P.A.

(57) ABSTRACT

A pressurizable implant, comprising a cylindrical body and at least one porous arm extending from and interconnected to the cylindrical body, the at least one porous arm being configured to accommodate a pressure gradient that is created by a device removably connectable to the cylindrical body.

18 Claims, 6 Drawing Sheets

(56) References Cited

U.S. PATENT DOCUMENTS

| | | |
|---|---|---|
| 6,261,322 B1 | 7/2001 | Despres, III et al. |
| 6,394,948 B1 | 5/2002 | Borst et al. |
| 6,494,916 B1 | 12/2002 | Babalola et al. |
| 6,607,561 B2 | 8/2003 | Brannon |
| 6,626,950 B2 | 9/2003 | Brown et al. |
| 6,740,120 B1 | 5/2004 | Grimes |
| 6,840,960 B2 | 1/2005 | Bubb |
| 6,979,336 B2 | 12/2005 | Durniak |
| 7,056,577 B1 | 6/2006 | Bruce et al. |
| 7,141,054 B2 | 11/2006 | Vandewalle |
| 7,217,283 B2 | 5/2007 | Pedrozo et al. |
| 7,445,640 B2 | 11/2008 | Despres, III et al. |
| 7,559,951 B2 | 7/2009 | DiSilvestro et al. |
| 7,608,062 B2 | 10/2009 | Sweeney |
| 7,879,100 B2 | 2/2011 | Denoziere et al. |
| 2003/0130742 A1 | 7/2003 | Connelly et al. |
| 2004/0133275 A1 | 7/2004 | Mansmann |
| 2004/0180072 A1 | 9/2004 | Tunc et al. |
| 2004/0193281 A1 | 9/2004 | Grimes |
| 2006/0015188 A1 | 1/2006 | Grimes |
| 2006/0069447 A1 | 3/2006 | DiSilvestro et al. |
| 2007/0083265 A1 | 4/2007 | Malone |
| 2008/0255560 A1 | 10/2008 | Myers et al. |
| 2009/0069899 A1 | 3/2009 | Klein |
| 2009/0259319 A1 | 10/2009 | DiSilvestro et al. |
| 2010/0268227 A1 | 10/2010 | Tong et al. |
| 2011/0218644 A1* | 9/2011 | Meridew et al. ........... 623/23.15 |

* cited by examiner

NEGATIVE-POSITIVE PRESSURIZABLE IMPLANT

CROSS-REFERENCE TO RELATED APPLICATIONS

This application is related and claims priority to U.S. Provisional Patent Application Ser. No. 61/533,374 filed on Sep. 12, 2011, the complete and entire disclosure of which is hereby expressly incorporated by reference herein.

TECHNICAL FIELD

The present invention generally relates to a pressurizable implant, at least a portion of which may be composed of a porous or mesh-like material, and more specifically to an implant adapted to create a pressure differential that is configured to encourage tissue ingrowth and/or to allow materials such as medicines, antibiotics, growth factors and blood platelets to be introduced at or around the implantation site.

BACKGROUND OF THE INVENTION

To promote and encourage the ingrowth of surrounding bony and soft tissues, biomedical implants sometimes contain one or more porous surface. In essence, these surfaces function as scaffolds, which provide desirable load-bearing strength at the implantation site as a result of the ingrown tissue.

While many implants have surfaces conducive to bony ingrowth, the depth of ingrowth penetration associated with these devices is not only limited by various biological factors, but is also limited by the fact that the ingrowth must be achieved without mechanical assistance. Moreover, in addition to promoting bony and soft tissue ingrowth, porous implants may also undesirably introduce microbes and metabolic agents into the implantation site, thereby increasing the potential for an infection to develop. Not only is the risk of infection increased, but the presence of toxins, wound drainage fluid and other substances within the implantation site may further hinder the positive effects of the ingrowth if they become trapped inside the porous material.

To minimize the increased threat of infection, biological pressure gradients are sometimes utilized during the surgical process. These pressure gradients not only enhance post-surgical recovery and healing (e.g., by assisting with wound closure and the application of suction forces for draining bodily fluids and exudates), but they also directly counter the onset of infectious conditions. Finally, they may also be used to irrigate wound sites by infusing them with pharmacological agents, such as medicines, antibiotics, growth factors and blood platelets.

The present invention is intended to improve upon and resolve some of these known deficiencies of the art.

SUMMARY OF THE INVENTION

In accordance with one aspect of the present invention, a pressurizable implant is provided and comprises a body and at least one porous arm extending from and interconnected to the body. The at least one porous arm is configured to accommodate a pressure gradient that is created by a device removably connectable to the body.

In accordance with another aspect of the present invention, a system for pressurizing an implant is provided. According to this aspect of the invention, the system comprises a body having an internal chamber, at least one porous arm extending from and interconnected to the internal chamber via a channel or duct, an airtight seal, and a device configured to removably couple to the airtight seal to distribute a pressure gradient across the at least one porous arm.

In accordance with still another aspect of the present invention, a method of distributing a pressure gradient across an implant during a surgical procedure is provided. According to this embodiment, the method comprises the steps of providing an implant having a body, an internal chamber and at least one porous arm extending from and interconnected to the internal chamber via a channel or duct; placing an airtight seal in the internal chamber; connecting a device to the airtight seal; and actuating the device to create a pressure differential across at least a portion of the implant.

Other objects and benefits of the invention will become apparent from the following written description along with the accompanying figures.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the specific methods and materials are now described. Moreover, the techniques employed or contemplated herein are standard methodologies well known to one of ordinary skill in the art and the materials, methods and examples are illustrative only and not intended to be limiting. Furthermore, while the present teachings for the disclosed pressurizable implant are sometimes described in association with a humeral head component and shoulder prosthesis, those skilled in the art will appreciate that the present teachings may be incorporated into various other orthopedic implants for a human body such as knee, hip, and other joints. Therefore, it is to be understood that the present illustrative embodiments are not meant to limit the present invention.

Figure 1:
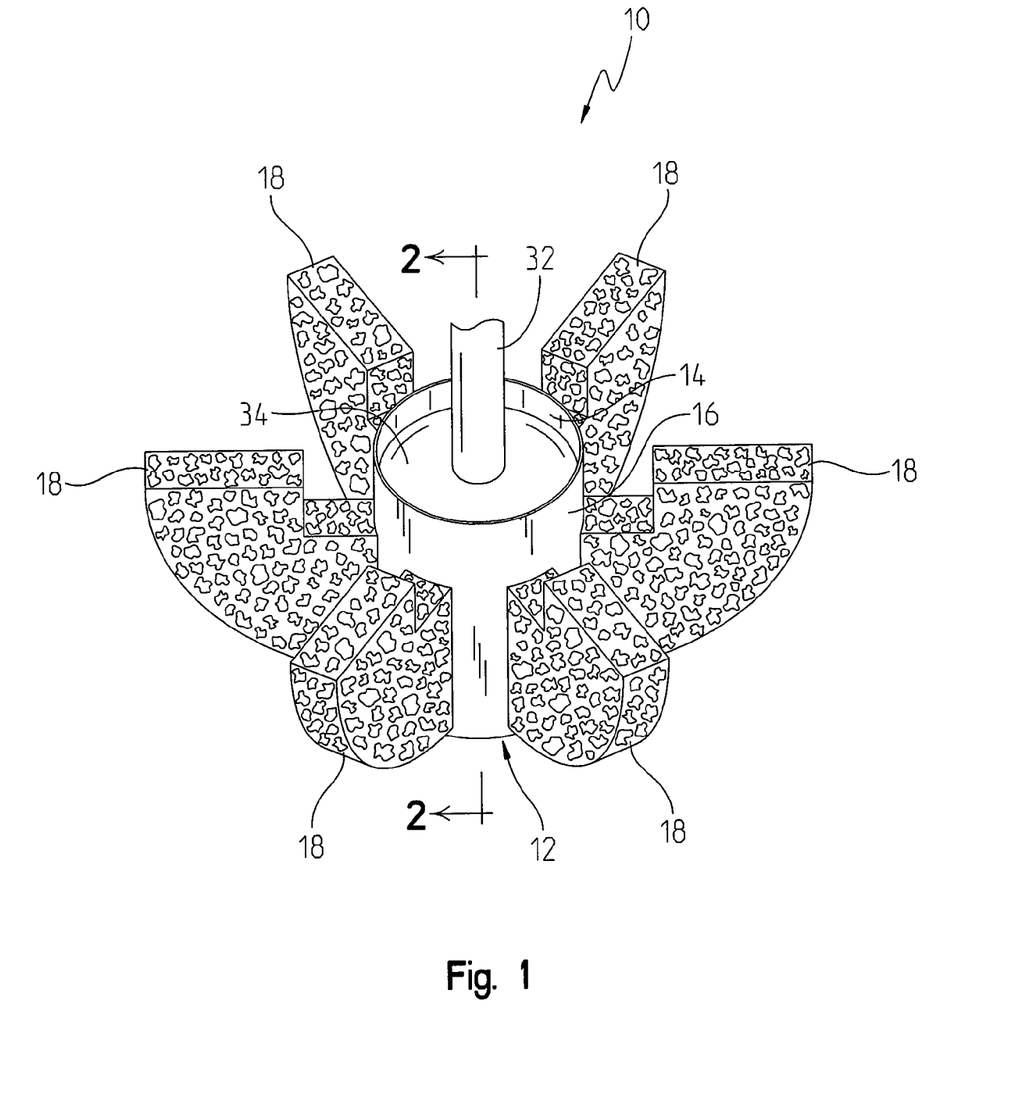
FIG. 1 is a perspective view of a pressurizable implant in accordance with the teachings of the present invention.

The following detailed description, beginning with FIG. 1, illustrates a pressurizable implant device constructed in accordance with the present teachings and generally identified by reference numeral 10. The pressurizable implant 10 is generally defined by a housing or body 12 that has an inner surface 14 and an outer surface 16. A plurality of arms or fins 18 are arranged around the outer surface 16 of the body 12, and, in accordance with certain embodiments, are formed entirely of a porous material that extends from the inner surface 14 of the body 12 to the outer surface 16. In certain specific embodiments, the porous material is comprised of a metal selected from one or more of stainless steel, titanium, titanium alloys, cobalt-chromium alloys and other materials that are suited for use in a biocompatible environment. While it should be understood and appreciated herein that the body 12 of the implant 10 may also be formed of a porous material, in accordance with certain aspects of the present invention, the body 12 is at least partially formed of a non-porous material, such as stainless steel, titanium, titanium alloys, cobalt-chromium alloys and other materials that are suited for use in a biocompatible environment. It should also be understood and appreciated herein that the size and shape of the implant can depend on the specific implantation procedure being conducted on the patient. In certain embodiments, however, the body 12 is cylindrical and has an opening at its top to accommodate an internal chamber 20.

Figure 2:
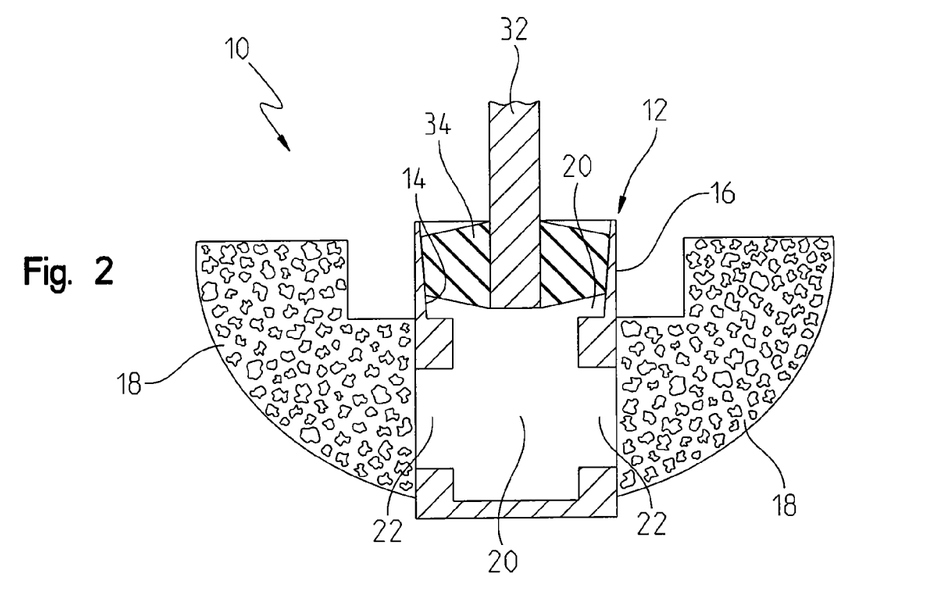
FIG. 2 is a front, cross-sectional view of the pressurizable implant taken along line 2-2 of FIG. 1.

Referring now to FIG. 2, a front, cross-sectional view of the pressurizable implant 10 taken along line 2-2 of FIG. 1 is shown. As can be appreciated from this illustration, the arms or fins 18 are interconnected to the internal chamber 20 of the body 12 by way of one or more channels or ducts 22. It should be understood herein that those of skill in the art can vary the specific size, number and orientation of the associated channels or ducts 22, particularly as these properties will largely be dependent upon the specific implantation procedure being performed. However, as will be discussed below, in accordance with certain aspects of the present invention, the channels or ducts 22 are sized so that they accommodate and facilitate the ingrowth of surrounding bony and soft tissues by allowing a pressure gradient to be created and distributed across the implant. In accordance with certain specific aspects of the present invention, the average pore size of the disclosed porous material may be from about 100 microns to about 700 microns, and the average porosity may be from about 40% to about 80%.

Figure 3:
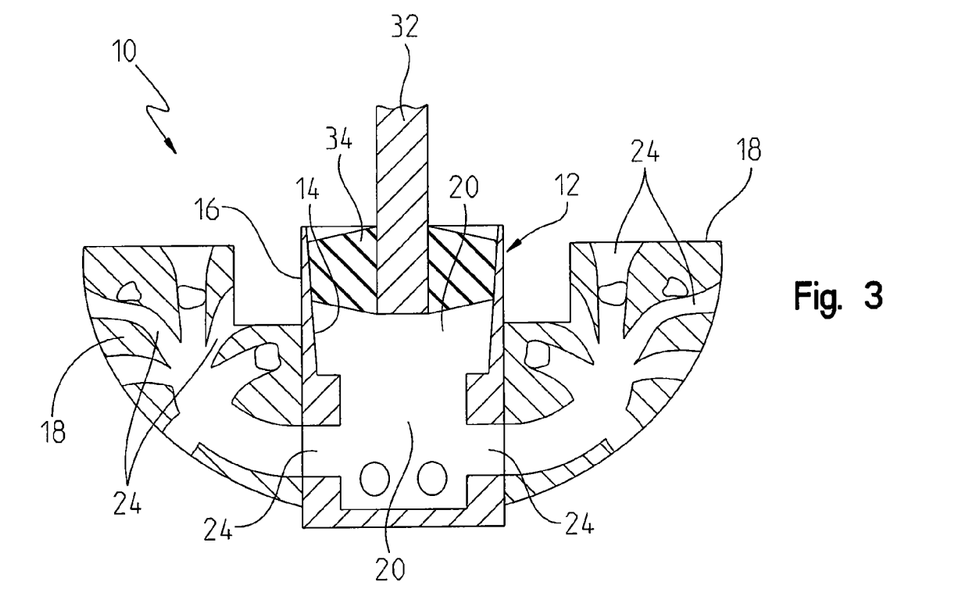
FIG. 3 is a front, cross-sectional view of another pressurizable implant in accordance with the teachings of the present invention.

FIG. 3 shows a front, cross-sectional view of another pressurizable implant 10 in accordance with the present invention. In accordance with this alternative aspect of the present invention, the plurality of arms or fins 18 are formed of a porous material, as well as include a series of branched channels 24 that extend from the inner surface 14 of the body 12 to the outer surface 16. In certain specific embodiments, the porous material is comprised of a metal selected from one or more of stainless steel, titanium, titanium alloys, cobalt-chromium alloys and other materials that are suited for use in a biocompatible environment. While it should be understood and appreciated herein that the arms or fins 18 of the implant 10 may be formed of a porous material, in accordance with certain aspects of the present invention, the arms or fins 18 may also be formed of a non-porous or partially porous material, wherein the branched channels 24 are etched or formed within the arms or fins 18 as desired. Those of skill in the art should understand and appreciate herein that one of the specific benefits of the branched channel configuration shown in FIG. 3 is that the channels 24 can be specifically designed to mimic the natural vascular shape and structure found within the human body. In addition, because the branched channels 24 can be designed to mimic specific orientations, it is possible to isolate where pharmacological agents are delivered into the body relative to these channels. To design the channels 24 in accordance with the teachings of the present invention, those of skill in the art will understand that known techniques such as additive manufacturing processes can be used.

Figure 4:
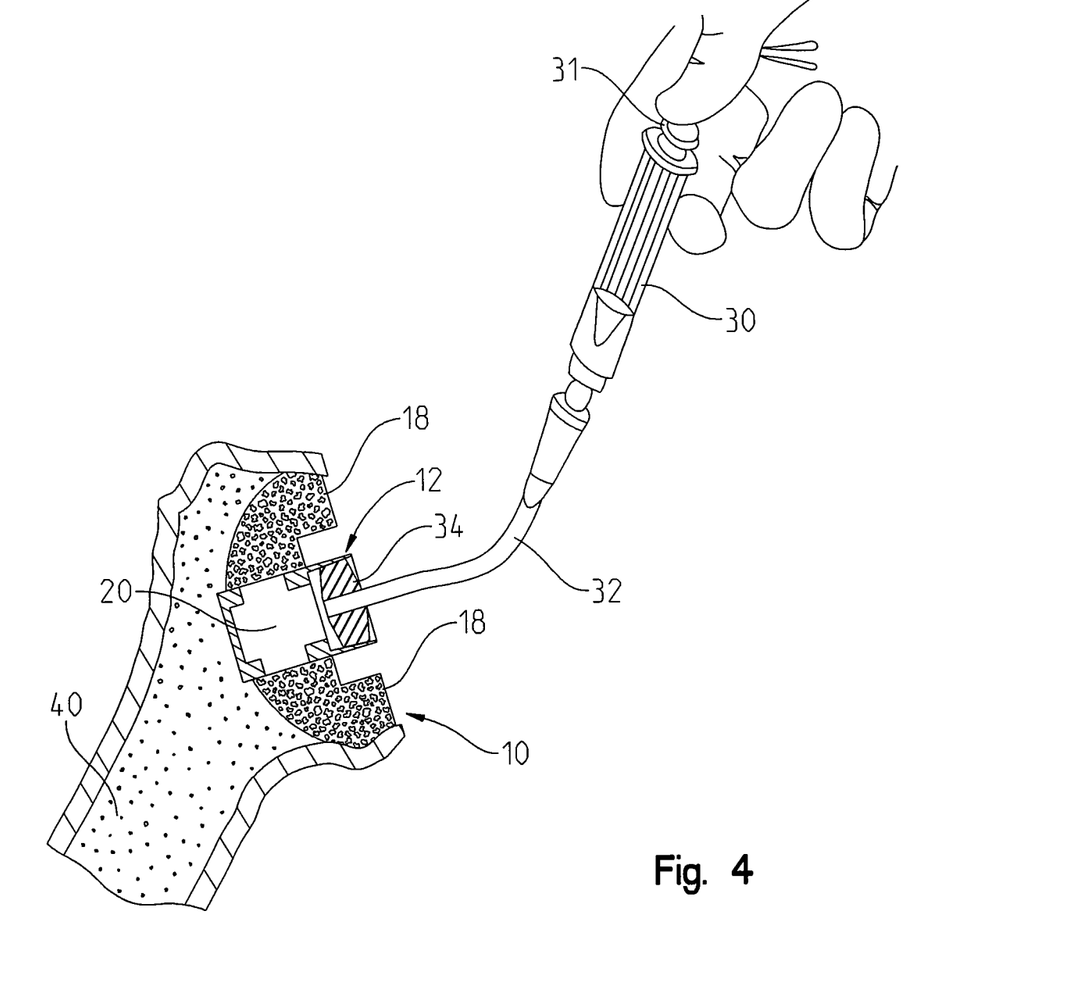
FIG. 4 is a cross-sectional view of an implanted pressurizable implant in accordance with the teaching of the present invention, the implant accommodating a pressure gradient as a user actuates a syringe connected to the implant.

With reference to FIG. 4, the arms or fins 18 of the present invention are configured to create and distribute a pressure differential or gradient by way of a device that is capable of altering the associated pressurization properties of the implant 10. Here, the implant device 10 is placed inside a humerus 40 as part of a shoulder procedure, and a syringe 30 is connected to the implant 10 device by way of a tube 32. To create and distribute a negative pressure gradient across the implant 10, a seal 34 (e.g., a rubber stopper or similar device) is placed inside or on top of the internal chamber 20 so that it seals against the inner surface 14 of the body 12, thereby creating an airtight seal. In turn, the tube 32 is advanced into a channel or bore that passes through the seal 34 and exits into the internal chamber 20. When a user actuates the plunger 31 of the syringe 30 by pulling it upward, air within the chamber 20 and the arms or fins 18 is removed, evacuated or sucked from the implant 10, thereby creating and distributing a negative pressure gradient across the implant 10 and its arms or fins 18. This negative pressure gradient created across the implant system facilitates and encourages (into the implant and its porous arms), the ingrowth of surrounding bony and soft tissues. Moreover, in the negative pressure gradient mode, fluid, toxins, microbes and other metabolic or biologic components can be drained from the implantation site, thereby reducing associated infection risks, as well as promoting post-surgical healing.

In addition to the negative pressure gradient mode, the present invention is also configured to create and distribute across the implant 10 a positive pressure gradient in accordance with certain embodiments. To create and distribute a positive pressure gradient across the implant 10, a seal 34 (e.g., a rubber stopper or similar device) is placed inside the internal chamber 20 so that it seals against the inner surface 14 of the body 12, thereby creating an airtight seal. In turn, a tube 32 is connected to a syringe 30 and then advanced into a channel or bore that passes through the seal 34 and then exits into the internal chamber 20. When a user actuates the plunger 31 of the syringe 30 by pushing it downward, liquid can be introduced into the chamber 20 and the arms or fins 18 and ultimately pushed out of the implant 10, thereby creating and distributing a positive pressure gradient across the implant 10 and its arms or fins 18. In a positive pressure gradient mode, the arms or fins 18 are configured to act as a manifold for distributing a pharmacological agent throughout the implantation site. In other words, the syringe 30 is capable of delivering a pharmacological agent through the airtight seal 34 and into the internal chamber 20, where the agent can in turn leach out into the arms or fins 18 to displace bodily fluids and toxins occupying the interstitial spaces in the arms and fins 18, thereby reducing or eliminating an environment in which microbes and metabolic products can develop and infect the implantation site. It should be understood and appreciated herein that various types of pharmacological agents can be used in accordance with the teachings of the present invention, including, but not limited to, one or more of medicines, antibiotics, growth factors and blood platelets.

As mentioned above, the biological pressure gradients that can be created in accordance with the present invention not only enhance post-surgical recovery and healing (e.g., by assisting with wound closure and the application of suction forces for draining bodily fluids and exudates), but they also directly counter the onset of infectious conditions. Moreover, the pressure gradients may also be used to irrigate wound sites by infusing them with the various pharmacological agents discussed above.

Figure 5:
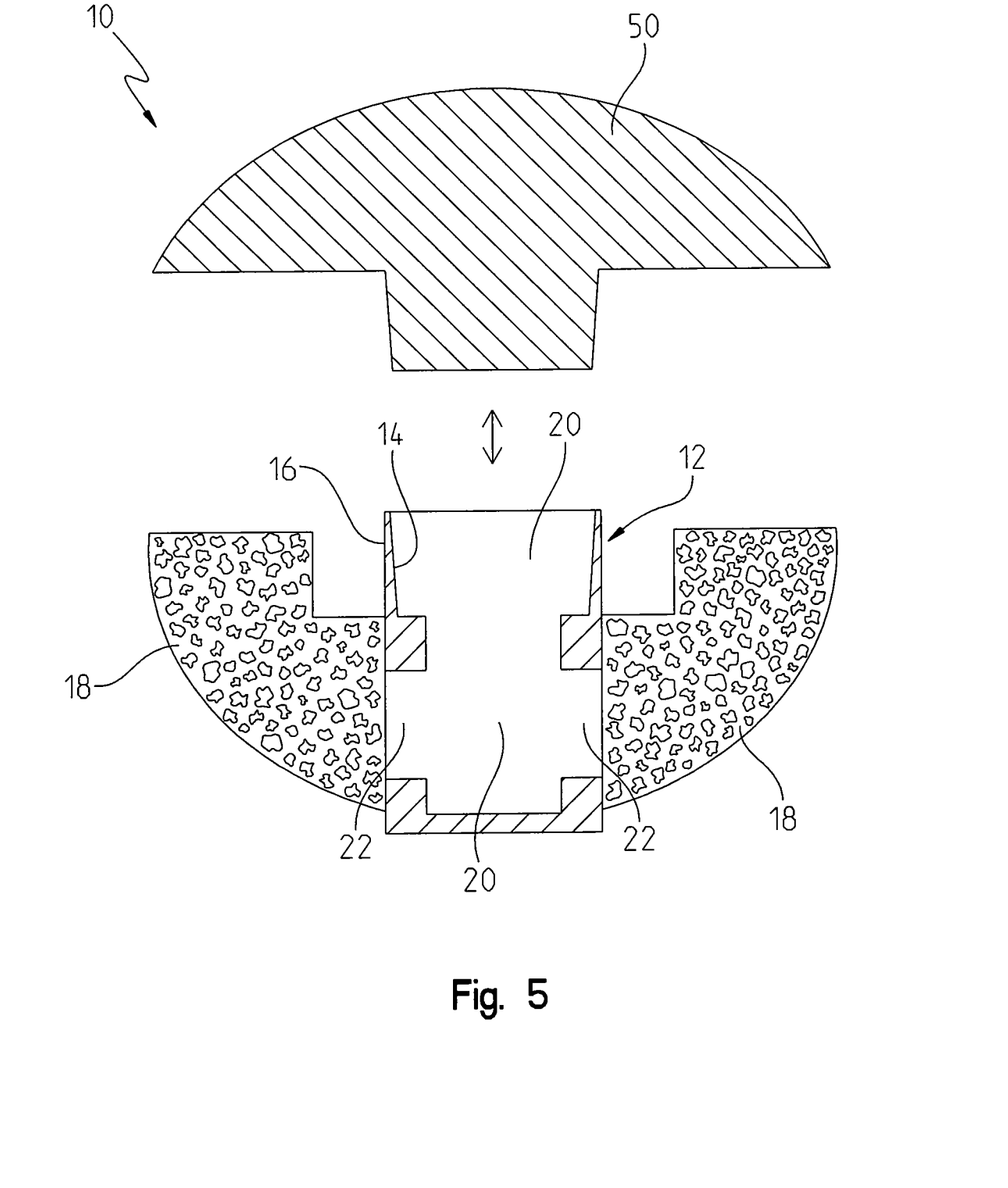
FIG. 5 is a front, cross-sectional view of a pressurizable implant in accordance with the present invention and having a humeral head component that is to be fitted into the implant during implantation.
Figure 6:
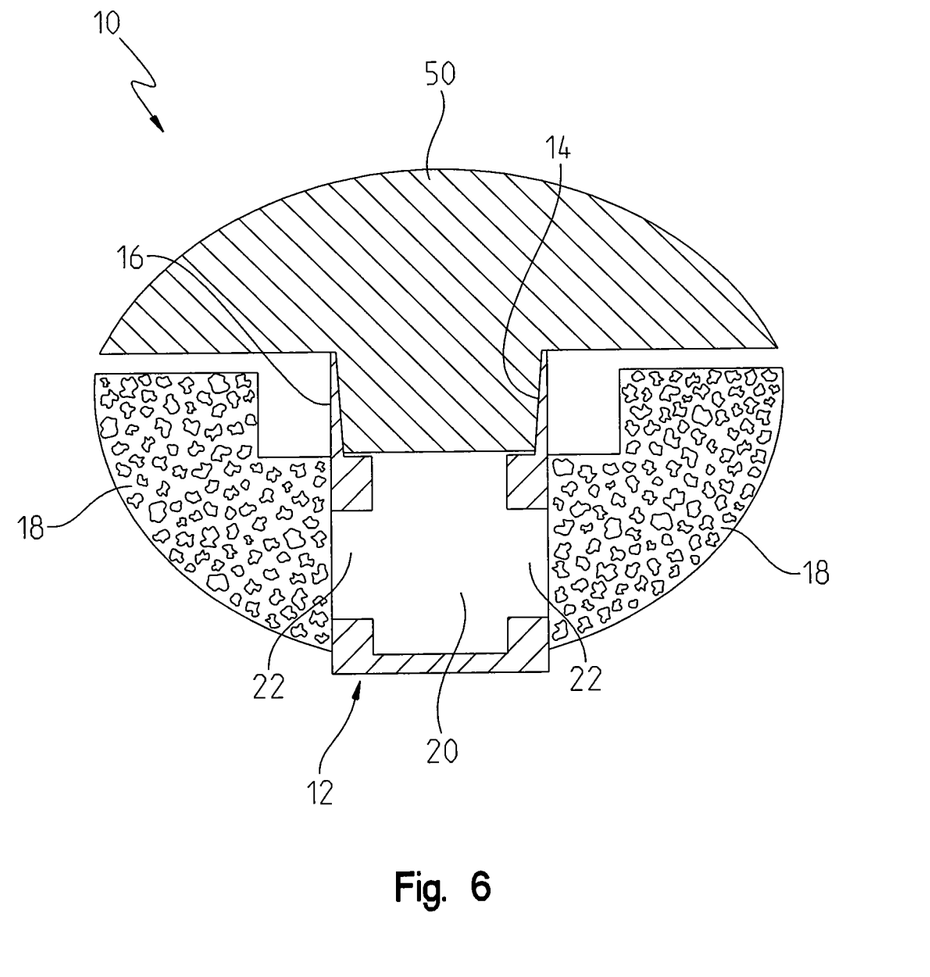
FIG. 6 is a front, cross-sectional view of the pressurizable implant of FIG. 5 after the humeral head component has been fitted into the implant.
Figure 7:
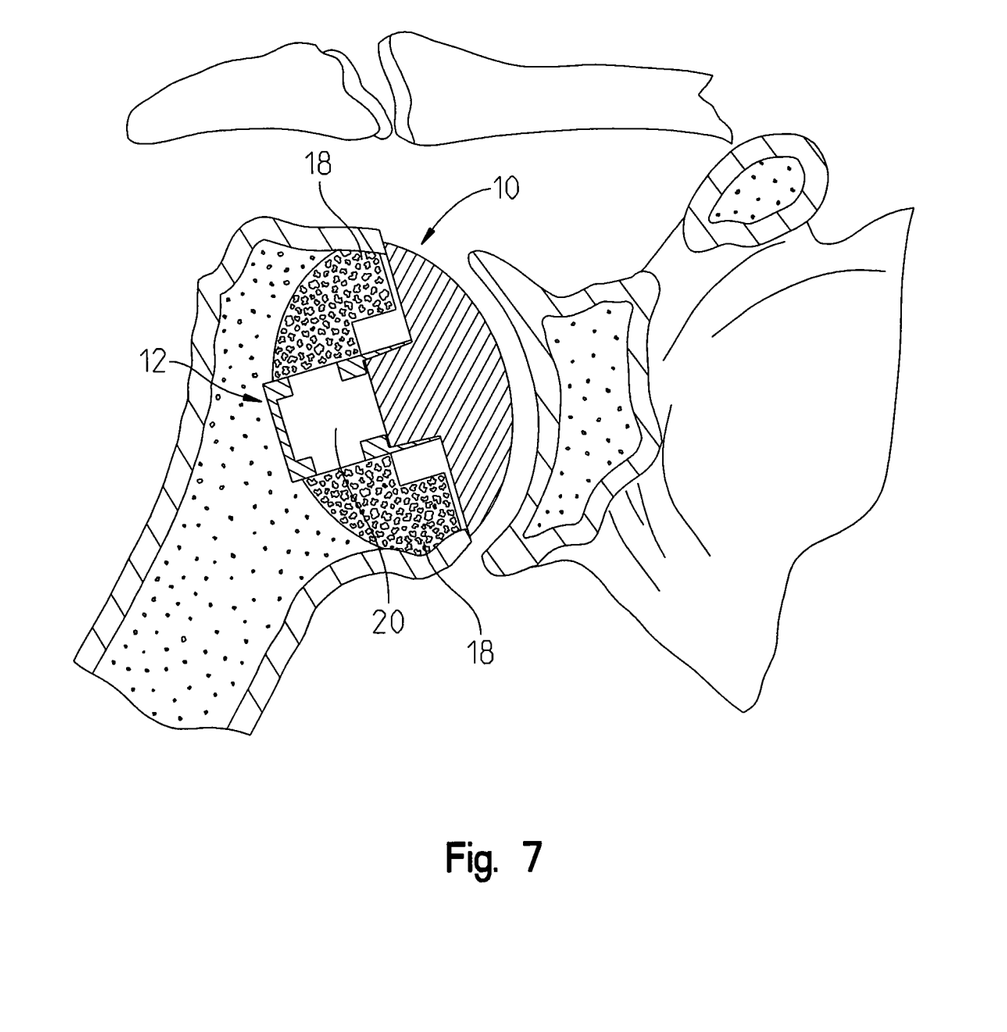
FIG. 7 is a cross-sectional view of a patient's shoulder having a pressurizable implant in accordance with the teachings of the present invention implanted therein together with a humeral head component.

As is also mentioned above, the disclosed pressurizable implants of the present invention are intended to be useful for various orthopedic procedures, including, but not limited to, shoulders, knees, hips, and various other joints. FIGS. 5-7, for instance, illustrate the use of the pressurizable implant device 10 as part of a stemless shoulder system. In accordance with this illustration, a humeral head component 50 is fitted inside a top portion of the internal chamber 20 of the body 12. In essence, the humeral head component 50 is shaped to fit into the same space that the airtight seal 34 would temporarily reside when a user is pressurizing the implant as described above. After the appropriate pressure gradient has been created and distributed across the implant, the humeral head component 50 is fitted into the implant (see FIG. 6) and then surgically implanted into the humerus 40 as a pressurized shoulder prosthesis (see FIG. 7).

It should be understood and appreciated herein that while the present disclosure includes various embodiments showing the biological pressure gradients being created with a standard syringe device, other devices capable of achieving a negative and/or positive pressure gradient may also be used including, but not limited to, standard operating room suction devices, air pumping apparatuses, vacuum devices, etc. Accordingly, the present invention is not intended to be limited herein.

It should also be understood and appreciated herein that in accordance with certain aspects of the present invention, it may be desirable to utilize a biological surface coating (e.g., a titanium porous plasma spray (PPS®) surface coating or a biomimetic coating (e.g., BoneMaster® coating), both of which are commercially available from Biomet), with the porous or nonporous surfaces to create a barrier to particulate debris (metallic, polyethylene or PMMA) and/or to further promote and increase the fixation of the bony ingrowth.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A pressurizable implant, comprising:
   a body shaped as a cylinder and defining a longitudinal axis; and
   a plurality of porous arms extending from and interconnected to the body at a single location along the longitudinal axis, the plurality of porous arms being configured to accommodate a pressure gradient that is created by a device removably connectable to the body, wherein at least one of the plurality of porous arms includes a biological surface coating disposed upon a surface thereof, the biological surface coating configured to promote the fixation of the pressurizable implant through enhancement of bony ingrowth.

2. The pressurizable implant of claim 1, wherein at least one of the plurality of porous arms is interconnected to the body via a channel or duct.

3. The pressurizable implant of claim 1, wherein the body includes an internal chamber that is configured to removably house an airtight seal.

4. The pressurizable implant of claim 3, wherein at least one of the plurality of porous arms is configured to accommodate a negative pressure gradient as a result of the device removing air through the airtight seal.

5. The pressurizable implant of claim 3, wherein at least one of the plurality of porous arms is configured to accommodate a positive pressure gradient as a result of the device delivering a pharmacological agent through the airtight seal, the pharmacological agent being selected from at least one of medicines, antibiotics, growth factors and blood platelets.

6. The pressurizable implant of claim 1, wherein the body is metallic.

7. The pressurizable implant of claim 1, wherein the device is a syringe.

8. A system for pressurizing an implant, comprising:
   a body shaped as a cylinder and defining a longitudinal axis, the body having an internal chamber;
   a plurality of porous arms extending from the body at a single location along the longitudinal axis, each of the plurality of porous arms being interconnected to the internal chamber via a channel or duct, wherein at least one of the plurality of porous arms includes a biological surface coating disposed upon a surface thereof, the biological surface coating configured to promote the fixation of the pressurizable implant through enhancement of bony ingrowth;
   an airtight seal; and
   a device configured to removably couple to the airtight seal to distribute a pressure gradient across the at least one porous arm.

9. The pressurizable implant system of claim 8, wherein the device is configured to distribute a negative pressure gradient across at least one of the plurality of porous arms as a result of the device removing air through the airtight seal.

10. The pressurizable implant system of claim 9, wherein the device is a syringe.

11. The pressurizable implant system of claim 8, wherein at least one of the plurality of porous arms is configured to accommodate a positive pressure gradient as a result of the device delivering a pharmacological agent through the airtight seal, the pharmacological agent being selected from at least one of medicines, antibiotics, growth factors and blood platelets.

12. The pressurizable implant system of claim 11, wherein the device is a syringe.

13. The pressurizable implant system of claim 8, wherein the body is metallic.

14. A pressurizable implant, comprising:
   a body shaped as a cylinder and defining a longitudinal axis, the body including an outer surface and an inner surface defining an internal chamber; and
   a plurality of arms interconnected to the body at a single location along the longitudinal axis, each of the plurality of arms:
   in contact with the outer surface of the body, extending externally of the internal chamber and away from the outer surface, and configured to accommodate a pressure gradient that is created by a device removably connectable to the body.

15. The pressurizable implant of claim 14, wherein the at least one arm includes a plurality of arms arranged around and in contact with the outer surface of the body.

16. The pressurizable implant of claim 15, wherein the body includes one or more channels, wherein each of the plurality of arms is coupled to one of the one or more channels.

17. The pressurizable implant of claim 16, wherein each of the plurality of arms includes a duct, wherein each of the ducts is operatively connected to the internal chamber through the one or more channels.

18. The pressurizable implant of claim 16, wherein each of the plurality of arms includes a biological surface coating disposed upon a surface thereof, the biological surface coating configured to promote the fixation of the pressurizable implant through enhancement of bony ingrowth.

* * * * *